United States Patent
Sejdic et al.

(10) Patent No.: US 10,869,629 B2
(45) Date of Patent: Dec. 22, 2020

(54) DEEP LEARNING FOR CLASSIFICATION OF SWALLOWS

(71) Applicant: UNIVERSITY OF PITTSBURGH—OF THE COMMONWEALTH SYSTEM OF HIGHER EDUCATION, Pittsburgh, PA (US)

(72) Inventors: Ervin Sejdic, Pittsburgh, PA (US);
Amro El-Jaroudi, Pittsburgh, PA (US);
James Coyle, Harmony, PA (US);
Joshua Dudik, Bethesda, MD (US);
Mingui Sun, Pittsburgh, PA (US);
Zhi-Hong Mao, Sewickley, PA (US)

(73) Assignee: University of Pittsburgh-Of die Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/323,556

(22) PCT Filed: Aug. 15, 2017

(86) PCT No.: PCT/US2017/046844
§ 371 (c)(1),
(2) Date: Feb. 6, 2019

(87) PCT Pub. No.: WO2018/035073
PCT Pub. Date: Feb. 22, 2018

(65) Prior Publication Data
US 2019/0167182 A1    Jun. 6, 2019

Related U.S. Application Data

(60) Provisional application No. 62/375,964, filed on Aug. 17, 2016.

(51) Int. Cl.
*A61B 5/00* (2006.01)
*G16H 50/20* (2018.01)
(Continued)

(52) U.S. Cl.
CPC .......... *A61B 5/4205* (2013.01); *G06K 9/6267* (2013.01); *G06N 3/0445* (2013.01);
(Continued)

(58) Field of Classification Search
None
See application file for complete search history.

(56) References Cited

U.S. PATENT DOCUMENTS 7,749,177 B2    7/2010  Chau et al.
8,267,875 B2    9/2012  Chau et al.
(Continued)

FOREIGN PATENT DOCUMENTS

WO    2016038585 A1    3/2016

OTHER PUBLICATIONS

Chen et al., Data Imputation Method Based on Deep Belief Network, 2015 IEEE International Conference on Computer and Information Technology; Ubiquitous Computing and Communications; Dependable, Autonomic and Secure Computing; Pervasive Intelligence and Computing; pp. 1238-1243 (Year: 2015).*

(Continued)

*Primary Examiner* — Alan Chen
(74) *Attorney, Agent, or Firm* — Eckert Seamans Cherin & Mellott, LLC; Philip E. Levy

(57) ABSTRACT

A method of classifying a swallow of a subject includes obtaining vibration data that is based on and indicative of a number of vibrations resulting from the swallow, and using a computer implemented deep learning classifier to classify the swallow based on the vibration data. Also, a system for classifying a swallow of a subject includes a computing (Continued)

device implementing a deep learning classifier. The computing device includes a processor apparatus structured and configured to receive vibration data that is based on and indicative of a number of vibrations resulting from the swallow, and use the deep learning classifier to classify the swallow based on the vibration data. The deep learning classifier may comprise a single layer or a multi-layer Deep Belief network.

18 Claims, 3 Drawing Sheets

(51) Int. Cl.
*G06N 3/08* (2006.01)
*G16H 40/63* (2018.01)
*G06N 3/04* (2006.01)
*G06K 9/62* (2006.01)

(52) U.S. Cl.
CPC ......... *G06N 3/0454* (2013.01); *G06N 3/0472* (2013.01); *G06N 3/08* (2013.01); *G06N 3/088* (2013.01); *G16H 40/63* (2018.01); *G16H 50/20* (2018.01); *A61B 2562/0219* (2013.01)

(56) References Cited

U.S. PATENT DOCUMENTS

| | | | |
|---|---|---|---|
| 8,992,446 B2 | 3/2015 | Chau et al. | |
| 9,138,171 B2 | 9/2015 | Chau et al. | |
| 9,687,191 B2 | 6/2017 | Chau et al. | |
| 2013/0184538 A1 | 7/2013 | Lee et al. | |
| 2014/0201126 A1 | 7/2014 | Zadeh et al. | |
| 2016/0026767 A1* | 1/2016 | Sarrafzadeh | A61B 5/6822 600/586 |

OTHER PUBLICATIONS

Dudik et al., A comparative analysis of DBSCAN, K-means, and quadratic variation algorithms for automatic identification of swallows from swallowing accelerometry signals; Computers in Biology and Medicine 59; 2015; pp. 10-18 (Year: 2015).*
Joon Lee et al., Classification of healthy and abnormal swallows based on accelerometry and nasal airflow signals; Artificial Intelligence in Medicine, 52 (2011) 17-25.
Ervin Sejdic et al., Classification of Penetration—Aspiration Versus Healthy Swallows Using Dual-Axis Swallowing Accelerometry Signals in Dysphagic Subjects; IEEE Transactions on Biomedical Engineering, vol. 60, No. 7, Jul. 2013.
Mohammad S. Nikjoo et al., Automatic discrimination between safe and unsafe swallowing using a reputation-based classifier, BioMedical Engineering OnLine 2011, 10:100.
Celeste Merey et al., Quantitative classification of pediatric swallowing through accelerometry, Journal of NeuroEngineering and Rehabilitation 2012, 9:34.
Joon Lee et al., A radial basis classifier for the automatic detection of aspiration in children with dysphagia, Journal of NeuroEngineering and Rehabilitation 2006, 3:14 doi:10.1186/1743-0003-3-14.
Joshua M. Dudik et al., Dysphagia and its effects on swallowing sounds and vibrations in adults, BioMed Eng OnLine (2018)17:69.
Yoshua Bengio, Learning Deep Architectures for AI, Foundations and Trends® in Machine Learning, vol. 2, No. 1 (2009) 1-127 © 2009 Y. Bengio, DOI: 10.1561/2200000006.
Iva Jestrovic et al., The effects of increased fluid viscosity on swallowing sounds in healthy adults, BioMedical Engineering OnLine 2013, 12:90.

* cited by examiner

DEEP LEARNING FOR CLASSIFICATION OF SWALLOWS

CROSS-REFERENCE TO RELATED APPLICATIONS

1011 This application is a U.S. National Stage Application under 35 U.S.C. § 371 of PCT International Application No. PCT/US2017/046844, entitled "Deep Learning for Classification of Swallows," filed on Aug. 15, 2017, and claims priority under 35 U.S.C. § 119(e) from U.S. provisional patent application No. 62/375,964, entitled "Deep Learning for Classification of Swallows" and filed on Aug. 17, 2016, the contents of which are incorporated herein by reference.

GOVERNMENT CONTRACT

This invention was made with government support under grant #s HD074819 and TR000005 awarded by the National Institutes of Health (NIH). The government has certain rights in the invention.

BACKGROUND OF THE INVENTION

1. Field of the Invention

The present invention relates to the diagnosis of dysphagia, and, in particular, to a method and apparatus for classifying the swallows of a subject using vibration data obtained from the swallows and a deep learning classifier, such as a Deep Belief network.

2. Description of the Related Art

Dysphagia is a term used to describe swallowing impairment. It is seen as a symptom of many conditions, but most commonly occurs as a result of neurological conditions such as physical trauma or stroke. Though typically not an immediate threat to a patient's well-being, dysphagia can quickly lead to more serious health complications including pneumonia, malnutrition, dehydration, and even death. The first attempt at identifying this condition in the clinic before these serious complications occur is a bedside assessment of the patient's actions and behavior while swallowing. Should this prove inconclusive or is deemed insufficient by the administering clinician, more complex instrumental examinations are utilized. Nasopharyngeal flexible endoscopic evaluations involve visualization of the pharynx and upper airway during oral intake, while videofluoroscopic assessment collects dynamic radiographic images of the oral cavity, pharynx, upper airway and proximal esophagus throughout the entire swallow event. The goal of these assessments is to determine the nature of swallowing pathophysiology, and determine appropriate methods of treatment more accurately than the current bedside assessments allow. However, both of these instrumental examinations require skilled expertise, specialized equipment, and a patient that is able to travel to the site of testing.

Multiple different swallowing screening tests have been investigated and implemented in the past. Non-instrumental methods, such as the 3 ounce water challenge, the Toronto bedside test, or the modified MASA, among others, have been widely implemented in the clinical setting. Though they generally have a high sensitivity for detecting aspiration, they have poor specificity and can lead to unnecessary interventions. Instrumentally-based screening methods have also produced mixed results, but efforts have been made to improve these methods and allow for their use alongside existing screening techniques. Cervical auscultation, in particular, has been studied in significant detail in recent years. Traditionally, this technique has utilized stethoscopes at the bedside to allow a clinician to listen to a patient swallow a bolus of liquid or food in real time. This non-instrumental screening method has not demonstrated adequate predictive value for swallowing disorders, but has given rise to a similar instrumental method in the form of digital microphones and accelerometers. In this digital form, any number of signal processing algorithms, such as those meant to filter noise or quantify statistical features, can be used to process the data. The result is a signal that is much cleaner and easier to analyze accurately and consistently than the human-interpreted signals obtained through non-digital techniques.

Past studies that have attempted to classify cervical auscultation signals have had certain limitations. First, many studies utilized relatively less than optimal sample sizes and did not clearly differentiate independent training and testing groups, which limits the generalizability of the results and increases the risk of over-fitting the model to the training data. In addition, most of these studies have classified their data based on the values of a set of pre-determined statistical features. While efforts were made to select only the most useful examples through genetic algorithms or other accepted methods in some studies, it is still possible that other researchers have artificially limited the classification potential of their method by limiting their selection of inputs. Likewise, the abundance of linear classifiers may have further biased the results of past studies and possibly reduced the maximum potential accuracy of the classification method. Finally, a number of studies incorporate measurements other than cervical auscultation, such as nasal airflow or tongue pressure. While there is nothing incorrect about this technique, it does introduce additional hardware and signals and complicates what is intended to be a simple task for the end user.

When investigating the literature related to swallowing classification, the present inventors have found that techniques that utilize neural network based classifiers have some of the highest reported accuracies for a given task. The present inventors have also found certain common areas of investigation or aspects of these techniques that could be improved upon. In particular, nearly all of these studies apply user-selected input features of a mathematically complex nature. The authors in J. Lee, et al., "A radial basis classifier for the automatic detection of aspiration in children with dysphagia," Journal of Neuro engineering and Rehabilitation, vol. 3, no. 14, pp. 1-17, July 2006, explore this topic and find that high-order features such as normality and dispersion ratio are only quadratically separable. The authors in M. Aboofazeli and Z. Moussavi, "Analysis and classification of swallowing sounds using reconstructed phase space features," in Proceedings of the IEEE International Conference on Acoustics, Speech, and Signal Processing, vol. 5, Philadelphia, Pa., Mar. 18-23, 2005, pp. 421-424, further support the necessity of such high-level investigation of swallowing vibrations and demonstrate the benefits of both nonlinear analysis techniques and neural networks with multiple hidden layers. While the higher-order analysis of swallowing signals demonstrates clear benefits, these studies acknowledge that they are investigating a limited selection of mathematical signal descriptions.

There is thus room for improvement in the field of swallowing classification.

SUMMARY OF THE INVENTION

In one embodiment, a method of classifying a swallow of a subject is provided. The method includes obtaining vibration data that is based on and indicative of a number of vibrations resulting from the swallow, and using a computer implemented deep learning classifier to classify the swallow based on the vibration data. The deep learning classifier may comprise a single layer or a multi-layer Deep Belief network.

In another embodiment, a system for classifying a swallow of a subject is provided that includes a computing device implementing a deep learning classifier. The computing device includes a processor apparatus structured and configured to receive vibration data that is based on and indicative of a number of vibrations resulting from the swallow, and use the deep learning classifier to classify the swallow based on the vibration data. The deep learning classifier may comprise a single layer or a multi-layer Deep Belief network.

In yet another embodiment, a system for classifying a swallow of a subject is provided. The system includes a data acquisition component structured and configured to obtain vibration data, the vibration data being based on and indicative of a number of vibrations resulting from the swallow, and a classification component structured and configured to implement a deep learning classifier and use the deep learning classifier to classify the swallow based on the vibration data. The deep learning classifier may comprise a single layer or a multi-layer Deep Belief network.

DETAILED DESCRIPTION OF EXEMPLARY EMBODIMENTS

Figure 1:
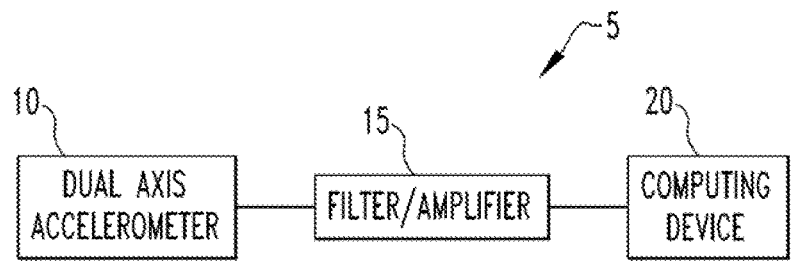
FIG. 1 is a block diagram of a system for classifying swallows according to a particular, non-limiting exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

As used herein, the term "approximately parallel" shall mean exactly parallel or ±10 degrees of exactly parallel.

As used herein, the term "approximately perpendicular" shall mean exactly parallel or ±10 degrees of exactly perpendicular.

As used herein, the term "deep learning classifier" shall mean a machine learning technique that categorizes a selection of data into one or more descriptive sets based on a transformation of the original data through a number of mathematical processing stages or layers.

As used herein, the term "Deep Belief network" shall mean an artificial neural network that employs a deep learning classifier that includes a number of hidden layers connected together consecutively (if multiple hidden layers are employed), where each hidden layer includes a restricted Boltzmann machine having neurons whose connections form a complete bipartite graph.

As used herein, the term "multi-layer Deep Belief network" shall mean a Deep Belief network having a plurality of hidden layers connected together consecutively, where each hidden layer includes a restricted Boltzmann machine having neurons whose connections form a complete bipartite graph.

As used herein, the term "single-layer Deep Belief network" shall mean a Deep Belief network having a single hidden layer, where the hidden layer includes a restricted Boltzmann machine having neurons whose connections form a complete bipartite graph.

As used herein, the term "hidden layer" shall mean a neural network layer of one or more neurons whose output is connected to the inputs of other neurons and that, as a result, is not visible as a network output.

As used herein, the temis "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

From previous attempts at classifying swallowing vibrations, the present inventors have determined that the field would benefit from a technique that is able to analyze higher-order signal features and that could self-select features to analyze through use of unsupervised learning methods. The disclosed concept, as described in greater detail herein, provides various embodiments of a method that allows for the differentiation of: (i) swallows made by a healthy subject, and (ii) swallows made by a dysphagic subject (e.g., without limitation, swallows that did not result in a significant amount of laryngeal penetration) using a relatively new classification technique known as deep learning. As described herein, the disclosed method may be performed using only cervical auscultation signals (e.g., vibration signals) that are obtained and/or recorded in a clinical environment during typical swallowing examination procedures. In a particular embodiment, the disclosed concept employs a particular classification technique, known as a Deep Belief network, that will provide more reliable classification than previously implemented techniques. The ability of a Deep Belief network to classify data in a non-linear manner based on higher order relationships as compared to a simple feed-forward neural network allows for the best possible swallowing classification. In one particular, non-limiting implementation, the Deep Belief network comprises an artificial neural network containing at least two hidden layers of neurons (each of which utilizes a restricted Boltzmann machine) whose connections formed a complete bipartite graph, with connections between the layers but not between units within each layer.

FIG. 1 is a block diagram of a system 5 for classifying swallows of a subject in which the method of the disclosed concept may be implemented according to one particular, non-limiting exemplary embodiment. System 5 includes a dual-axis accelerometer 10 (e.g., the ADXL322 sold by Analog Devices) which is structured to be attached to a subject's neck (e.g., anterior to the cricoid cartilage) using a suitable connection method such as, without limitation, double-sided tape. In the exemplary embodiment, dual-axis accelerometer 10 is attached such that the axes of acceleration are aligned to the superior-inferior (S-I) and the anterior-posterior (A-P) directions. More particularly, in the exemplary embodiment, the first axis of dual-axis accelerometer 10 is aligned approximately parallel to the subject's cervical spine and the second axis of the dual-axis accelerometer 10 is aligned approximately perpendicular to the subject's coronal plane. System 5 also includes a filter/amplifier 15 which receives the output of dual-axis accelerometer 10, and a computing device 20 (described below) coupled to the output of filter/amplifier 15. In such a configuration, vibration data generated by dual-axis accelerometer 10 is band-pass filtered and amplified by filter/amplifier 15 (e.g., with a pass band of 0.1-3000 Hz in the exemplary embodiment), and the filtered and amplified vibration data is then sampled (e.g., without limitation, at 20 kHz) by computing device 20 (e.g., using a custom LabVIEW program running on computing device 20).

Computing device 20 may be, for example, and without limitation, a PC, a laptop computer, a tablet computer, a smartphone, or any other suitable computer processing device structured and configured to perform the functionality described herein. Computing device 20 is structured and configured to receive the filtered and amplified vibration data output by filter/amplifier 15 and process the filtered and amplified vibration data using an embodiment of the method described in detail herein in order to classify swallows from the subject. In the exemplary embodiment, the signals recorded with and output by dual-axis accelerometer 10 and filtered and amplified by filter/amplifier 15 undergo several digital processing steps in computing device 20 to improve their quality. In particular, in the non-limiting exemplary embodiment, FIR filters are utilized to remove the noise inherent in recording devices such as dual-axis accelerometer 10, and wavelet denoising techniques are utilized to reduce the effects of white noise. Spline filtering techniques are also employed in order to remove low frequency artifacts such as head motion.

Figure 2:
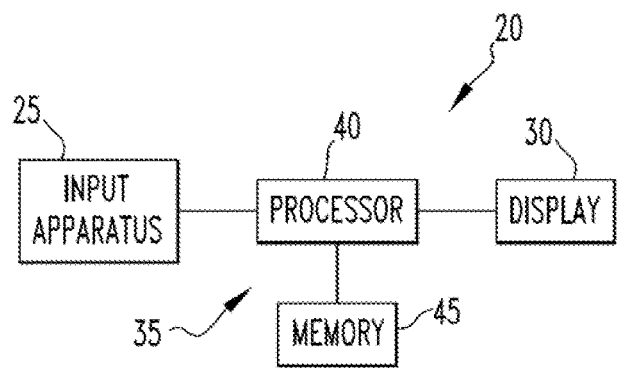
FIG. 2 is a block diagram of a computing device forming a part of the system of FIG. 1 according to one exemplary embodiment.

FIG. 2 is a block diagram of computing device 20 according to one particular exemplary embodiment. As seen in FIG. 2, the exemplary computing device 20 is a PC or laptop computer and includes an input apparatus 25 (which in the illustrated embodiment is a keyboard), a display 30 (which in the illustrated embodiment is an LCD), and a processor apparatus 35. A user is able to provide input into processor apparatus 35 using input apparatus 25, and processor apparatus 35 provides output signals to display 30 to enable display 30 to display information to the user, such as, without limitation, a swallow classification generated using the method of the present invention. Processor apparatus 35 comprises a processor 40 and a memory 45. Processor 40 may be, for example and without limitation, a microprocessor (μP), a microcontroller, or some other suitable processing device, that interfaces with memory 45. Memory 45 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 45 has stored therein a number of routines that are executable by processor 40. One or more of the routines implement (by way of computer/processor executable instructions) at least one embodiment of the method discussed in detail herein for classifying subject swallows using vibration data. In particular, in the exemplary embodiment, the one or more routines implement one or more embodiments of a Deep Belief network as described herein.

Figure 3:
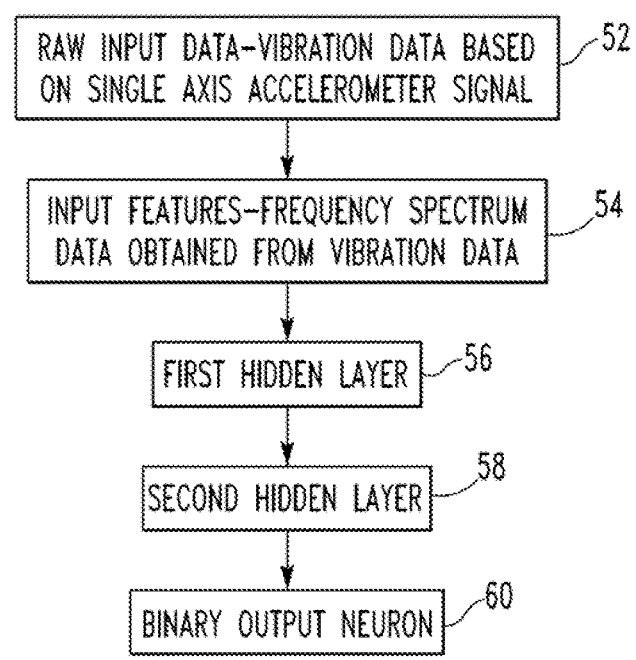
FIG. 3 is a schematic diagram of a multi-layer Deep Belief network according to one particular exemplary embodiment of the disclosed concept.

FIG. 3 is a schematic diagram of a multi-layer Deep Belief network 50 that may be implemented by computing device 20 according to one particular exemplary embodiment of the disclosed concept. Multi-layer Deep Belief network 50 uses accelerometer data from a single axis, such as the A-P or S-I axis as described herein. Referring to FIG. 3, multi-layer Deep Belief network 50 includes a raw input data layer 52. The raw input data in raw input data layer 52 is vibration data based on a single axis signal from dual axis accelerometer 10 (the A-P or S-I axis). Multi-layer Deep Belief network 50 further includes an input feature layer 54. The input features of input feature layer 54 comprise frequency spectrum data obtained from the vibration data of raw input data layer 52. In the exemplary embodiment, the frequency spectrum data comprises the Fourier transform of each segmented swallowing vibration captured by dual axis accelerometer 10. As seen in FIG. 3, Multi-layer Deep Belief network 50 also further includes a first hidden layer 56 that receives the outputs from input feature layer 54 and a second hidden layer 58 that is connected consecutively to first hidden layer 56 and receives the outputs of first hidden layer 56. As noted elsewhere herein, first hidden layer 56 and second hidden layer 58 each comprises a restricted Boltzmann machine having neurons whose connections form a complete bipartite graph. Finally, multi-layer Deep Belief network 50 includes a classification portion in the form of a binary output neuron 60. Binary output neuron 60 is structured and configured to receive the outputs of second hidden layer 58 and to generate a binary output that indicates whether the input data (raw input data layer 52) corresponds to a dysphagic (e.g., logic 1) or healthy (e.g., logic 0) swallow. In the exemplary embodiment, binary output neuron 60 is a one-hot encoded neuron.

Figure 4:
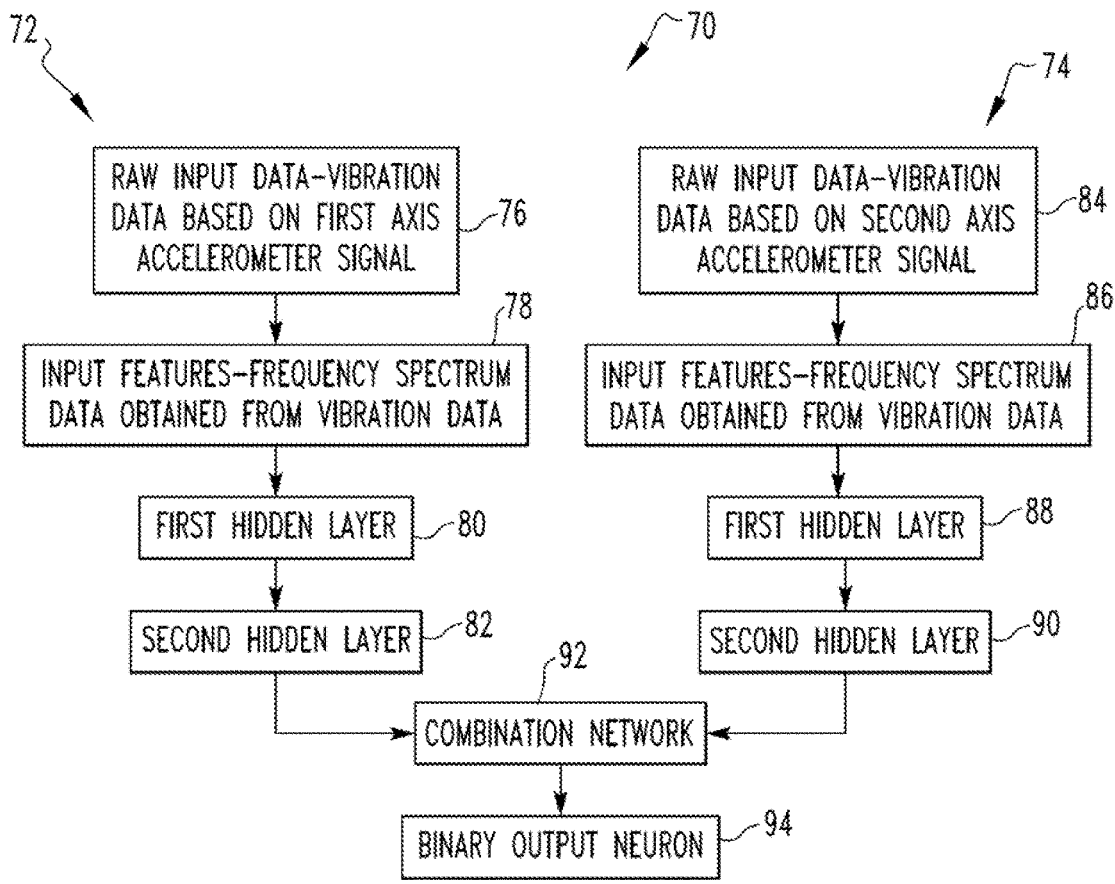
FIG. 4 is a schematic diagram of a combined multi-layer Deep Belief network according to another particular exemplary embodiment of the disclosed concept.

FIG. 4 is a schematic diagram of a combined multi-layer Deep Belief network 70 that may be implemented by computing device 20 according to another particular exemplary embodiment of the disclosed concept. Combined multi-layer Deep Belief network 70 uses accelerometer data from a two axes, such as the A-P and S-I axes as described herein. In addition, referring to FIG. 4, combined multi-layer Deep Belief network 70 includes three stages. In particular, and as described in greater detail below, combined multi-layer Deep Belief network 70 includes a first stage that comprises two independent multi-layer Deep Belief networks of equal size that each operate on one vibration signal (one axis), a second stage that comprises a combination network of one, two or three layers (each a hidden layer) that combines the outputs of the independent multi-layer Deep Belief networks of the first stage, and a third stage that makes a classification based on the output of the second stage.

More specifically, as seen in FIG. 4, combined multi-layer Deep Belief network 70 includes a first multi-layer Deep Belief network portion 72 and a second multi-layer Deep Belief network portion 74 (together forming the first stage). First multi-layer Deep Belief network portion 72 includes a raw input data layer 76. The raw input data in raw input data layer 76 is vibration data based on a first axis signal from dual axis accelerometer 10 (e.g., the A-P axis). First multi-layer Deep Belief network portion 72 further includes an input feature layer 78, wherein the input features comprise frequency spectrum data (e.g., the Fourier transform of each segmented swallowing vibration) obtained from the vibration data of raw input data layer 76. First multi-layer Deep Belief network portion 72 also further includes a first hidden layer 80 that receives the outputs from input feature layer 78 and a second hidden layer 82 that is connected consecutively to first hidden layer 80 and receives the outputs of first hidden layer 80. As noted elsewhere herein, first hidden layer 80 and second hidden layer 82 each comprises a restricted Boltzmann machine having neurons whose connections form a complete bipartite graph. Similarly, second multi-layer Deep Belief network portion 74 includes a raw input data layer 84. The raw input data in raw input data layer 84 is vibration data based on a second axis signal from dual axis accelerometer 10 (e.g., the S-I axis). Second multi-layer Deep Belief network portion 74 further includes an input feature layer 86, wherein the input features comprise frequency spectrum data (e.g., the Fourier transform of each segmented swallowing vibration) obtained from the vibration data of raw input data layer 84. Second multi-layer Deep Belief network portion 74 also further includes a first hidden layer 88 that receives the outputs from input feature layer 86 and a second hidden layer 90 that is connected consecutively to first hidden layer 88 and receives the outputs of first hidden layer 88. As noted elsewhere herein, first hidden layer 88 and second hidden layer 90 each comprises a restricted Boltzmann machine having neurons whose connections form a complete bipartite graph.

As seen in FIG. 4, combined multi-layer Deep Belief network 70 further includes combination network 92 (the second stage) which, in the exemplary embodiment, comprises a neural network having one, two, or three hidden layers. Combination network 92 is structured configured to receive the outputs of second hidden layer 82 and second hidden layer 90 of first and second multi-layer Deep Belief network portions 72 and 74, respectively. Combined multi-layer Deep Belief network 70 also further includes a binary output neuron 94 (the third stage) that is similar in structure and configuration to binary output neuron 60 described elsewhere herein.

As will be appreciated, combined multi-layer Deep Belief network 70 allows each individual axis input to be processed by its own respective multi-layer deep belief network before being combined. As a result, combined multi-layer Deep Belief network 70 is better able to identify interactions at higher-orders.

Figure 5:
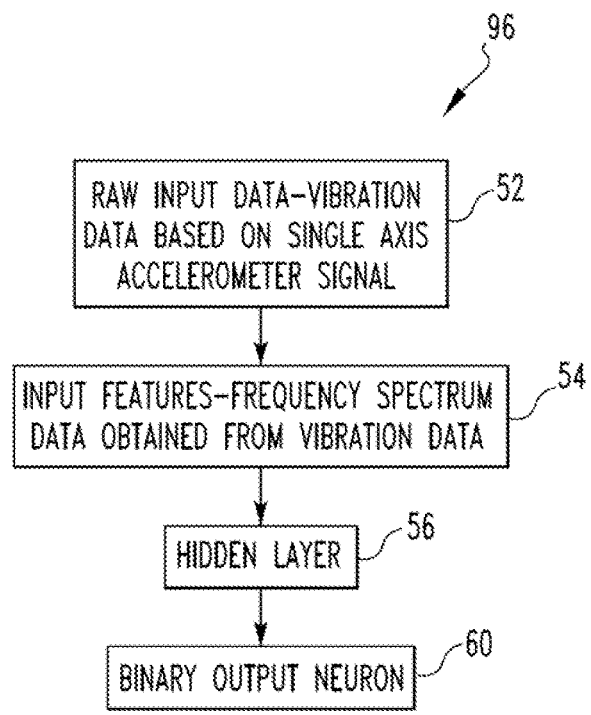
FIG. 5 is a schematic diagram of a single-layer Deep Belief network according to another particular exemplary embodiment of the disclosed concept.

FIG. 5 is a schematic diagram of a single-layer Deep Belief network 96 that may be implemented by computing device 20 according to still another particular exemplary embodiment of the disclosed concept. Single-layer Deep Belief network 96 is similar to multi-layer Deep Belief network 50, and like components are labeled with like reference numerals. However, single-layer Deep Belief network 96, unlike multi-layer Deep Belief network 50, is implemented in the form of a Deep Belief network that includes only a single hidden layer 56.

Figure 6:
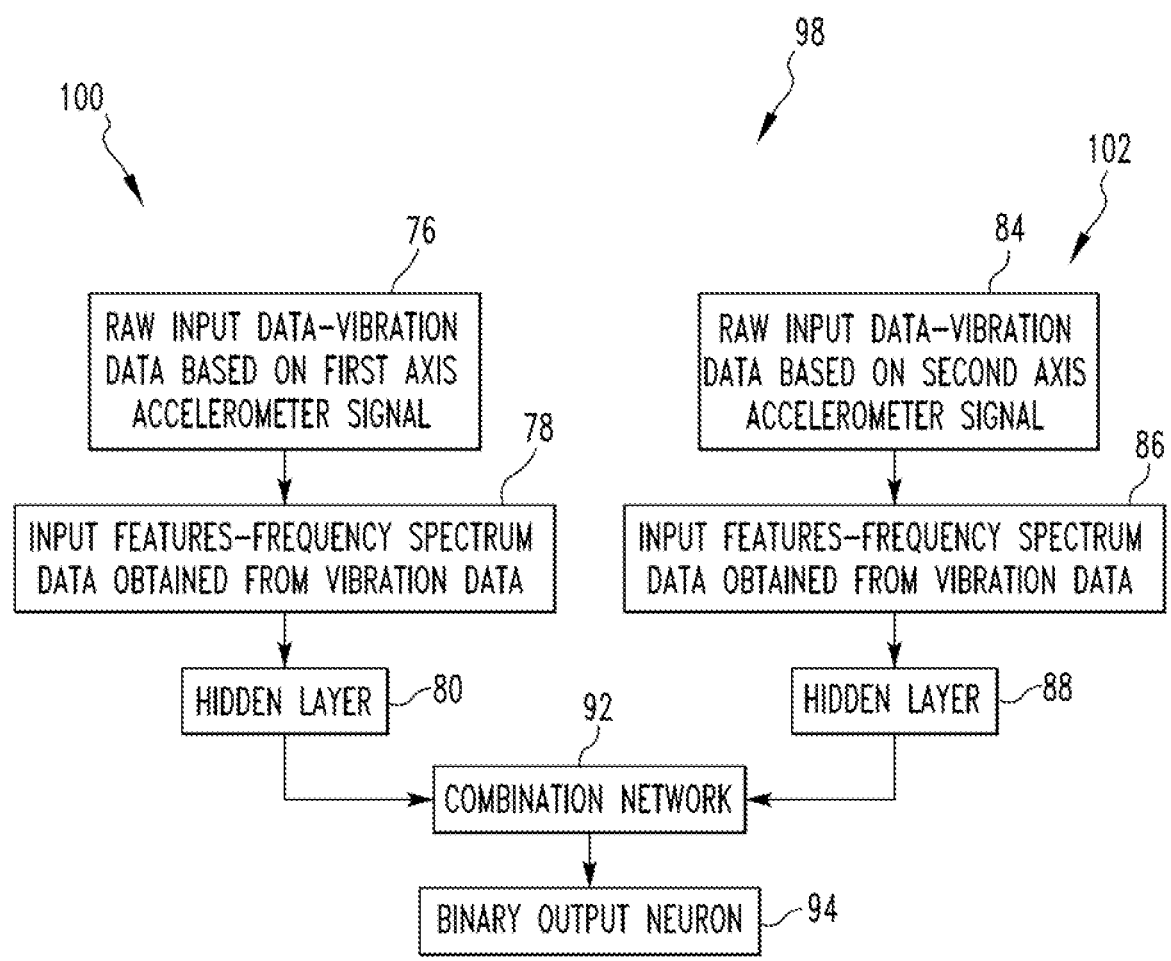
FIG. 6 is a schematic diagram of a combined single-layer Deep Belief network according to still another particular exemplary embodiment of the disclosed concept.

FIG. 6 is a schematic diagram of a combined single-layer Deep Belief network 98 that may be implemented by computing device 20 according to yet another particular exemplary embodiment of the disclosed concept. Combined single-layer Deep Belief network 98 is similar to combined multi-layer Deep Belief network 70, and like components are labeled with like reference numerals. As seen in FIG. 6, combined single-layer Deep Belief network 98, like combined multi-layer Deep Belief network 70, employs three stages. However, in combined single-layer Deep Belief network 98, the first stage comprises a first single-layer Deep Belief network portion 100 wherein the input data is based on a first axis signal from dual axis accelerometer 10 (e.g., the A-P axis) and a second single-layer Deep Belief network portion 102 wherein the input data is based on a second axis signal from dual axis accelerometer 10 (e.g., the S-I axis).

According to one non-limiting exemplary embodiment, each Deep Belief network is trained in a fine-tuning stage using supervised learning and backpropagation algorithms. However, backpropagation is not always the most effective method of training an entire multi-layered network due to the vanishing gradient problem. Therefore, as an alternative, each hidden layer (restricted Boltzmann machine) described herein is partially trained as it is built in a pre-training stage by using an unsupervised learning method. Specifically, in the exemplary embodiment, pre-training is conducted in a greedy, layerwise fashion by implementing the contrastive divergence algorithm. This algorithm performs block Gibbs sampling within a gradient descent procedure and attempts to minimize the negative log-likelihood of the training data.

In one particular, non-limiting exemplary embodiment, Bernoulli restricted Boltzmann machines are used to implemented each Deep Belief network described herein. In addition, a learning rate of 0.05 is used in this particular exemplary embodiment for each of the Bernoulli restricted Boltzmann machines. This was found, through trial and error, to provide a relatively steady and non-chaotic rate of weight adjustment for the size of the training set. It also demonstrated a minimal amount of over-tuning of the model when the networks are tested with the training data set. Moreover, in this particular exemplary embodiment, logistic sigmoid activation functions are used for all of the neurons in the Deep Belief networks. This function is smooth, differentiable, and positive at all points which should minimize any potential difficulties with implementing training algorithms. Also, the log-likelihood of the data was chosen as the cost function for the unsupervised training in order to simplify the algorithmic implementation of the network's training while mean squared error was used in the final supervised learning stage to simplify the interpretation of the network's behavior.

Moreover, in the particular exemplary embodiments described in detail herein, the deep learning classifier that is used is a Deep Belief network. It will be understood, however, that other types and/or styles of deep learning classifiers may also be employed within the scope of the disclosed concept including, without limitation, convolutional neural networks, long short-term memory networks, and stacked auto-encoders, among others.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of classifying a swallow of a subject, comprising:
   obtaining vibration data, the vibration data being based on and indicative of a number of vibrations resulting from the swallow; and
   using a computer implemented deep learning classifier to classify the swallow based on the vibration data;
   wherein the vibration data is dual-axis data indicative of vibrations resulting from the swallow in a first axis and a second axis, wherein the vibration data comprises first axis vibration data indicative of the vibrations in the first axis and second axis vibration data indicative of the vibrations in the second axis, and wherein the deep learning classifier comprises a first Deep Belief network, a second Deep Belief network, and a combination network, wherein the first Deep belief network uses the first axis vibration data and the second Deep Belief network uses the second axis vibration data.

2. The method according to claim 1, wherein the first axis is aligned approximately parallel to the subject's cervical spine and the second axis is aligned approximately perpendicular to the subject's coronal plane.

3. The method according to claim 1, wherein the first Deep Belief network is a multi-layer Deep Belief network and the second Deep Belief network is a multi-layer Deep Belief network.

4. The method according to claim 1, wherein the vibration data is generated from data produced by an accelerometer.

5. The method according to claim 4, wherein the vibration data comprises a Fourier transform of processed accelerometer data, and wherein the processed accelerometer data is generated by processing the data produced by the accelerometer.

6. The method according to claim 1, wherein the first and second Deep Belief networks are trained using at least one of supervised learning and unsupervised learning.

7. The method according to claim 6, wherein the first and second Deep Belief networks are trained using supervised learning and unsupervised learning, wherein the unsupervised learning is conducted in a greedy, layerwise fashion by implementing a contrastive divergence algorithm.

8. The method according to claim 7, wherein the contrastive divergence algorithm is a stepwise contrastive divergence algorithm.

9. A computer program product, comprising a non-transitory computer usable medium having a computer readable program code embodied therein, the computer readable program code being adapted to be executed to implement a method of classifying a swallow of a subject as recited in claim 1.

10. A system for classifying a swallow of a subject, comprising:
    a computing device implementing a deep learning classifier, the computing device having a processor apparatus structured and configured to:
    receive vibration data, the vibration data being based on and indicative of a number of vibrations resulting from the swallow; and
    use the deep learning classifier to classify the swallow based on the vibration data,
    wherein the vibration data is dual-axis data indicative of vibrations resulting from the swallow in a first axis and a second axis, wherein the vibration data comprises first axis vibration data indicative of the vibrations in the first axis and second axis vibration data indicative of the vibrations in the second axis, and wherein the deep learning classifier comprises a first Deep Belief network, a second Deep Belief network, and a combination network, wherein the first Deep belief network uses the first axis vibration data and the second Deep Belief network uses the second axis vibration data.

11. The system according to claim 10, further comprising an accelerometer coupled to the computing device, the accelerometer being structured to generate first axis accelerometer data based on the vibrations resulting from the swallow in the first axis and second axis accelerometer data based on the vibrations resulting from the swallow in the second axis, wherein the first axis vibration data is based on the first axis accelerometer data and the second axis vibration data is based on the second axis accelerometer data.

12. The system according to claim 11, wherein the first axis is aligned approximately parallel to the subject's cervical spine and the second axis is aligned approximately perpendicular to the subject's coronal plane.

13. The system according to claim 10, wherein the first Deep Belief network is a multi-layer Deep Belief network and the second Deep Belief network is a multi-layer Deep Belief network.

14. The system according to claim 10, wherein the vibration data comprises a Fourier transform of processed accelerometer data, and wherein the processed accelerometer data is generated by processing the data produced by the accelerometer.

15. The system according to claim 10, wherein the first and second Deep Belief networks are trained using at least one of supervised learning and unsupervised learning.

16. The system according to claim 15, wherein the first and second Deep Belief networks are trained using supervised learning and unsupervised learning, wherein the unsupervised learning is conducted in a greedy, layerwise fashion by implementing a contrastive divergence algorithm.

17. The system according to claim 16, wherein the contrastive divergence algorithm is a stepwise contrastive divergence algorithm.

18. A system for classifying a swallow of a subject, comprising:
- a data acquisition component structured and configured to obtain vibration data, the vibration data being based on and indicative of a number of vibrations resulting from the swallow; and
- a classification component structured and configured to implement a deep learning classifier and use the deep learning classifier to classify the swallow based on the vibration data;
- wherein the vibration data is dual-axis data indicative of vibrations resulting from the swallow in a first axis and a second axis, wherein the vibration data comprises first axis vibration data indicative of the vibrations in the first axis and second axis vibration data indicative of the vibrations in the second axis, and wherein the deep learning classifier comprises a first Deep Belief network, a second Deep Belief network, and a combination network, wherein the first Deep belief network uses the first axis vibration data and the second Deep Belief network uses the second axis vibration data.

* * * * *